United States Patent
Barkan et al.

(10) Patent No.: US 6,578,767 B1
(45) Date of Patent: Jun. 17, 2003

(54) LOW COST BAR CODE READER

(75) Inventors: Ed Barkan, Miller Place, NY (US); Howard Shepard, Great River, NY (US)

(73) Assignee: Symbol Technologies, Inc., Holtsville, NY (US)

( * ) Notice: Subject to any disclaimer, the term of this patent is extended or adjusted under 35 U.S.C. 154(b) by 149 days.

(21) Appl. No.: 09/616,564

(22) Filed: Jul. 14, 2000

Related U.S. Application Data (60) Provisional application No. 60/144,657, filed on Jul. 16, 1999.

(51) Int. Cl.[7] .................................................. G06K 7/10
(52) U.S. Cl. .............................. 235/462.43; 235/462.3; 235/462.2; 235/462.21; 235/462.22
(58) Field of Search ........................... 235/462.3, 462.2, 235/462.21, 462.22, 462.43

(56) References Cited

U.S. PATENT DOCUMENTS

| | | | |
|---|---|---|---|
| 4,387,297 A | | 6/1983 | Swartz et al. ................ 235/462 |
| 4,760,248 A | | 7/1988 | Swartz et al. ................ 235/472 |
| 4,906,843 A | * | 3/1990 | Jones et al. .................. 250/221 |
| 5,142,131 A | * | 8/1992 | Collins, Jr. et al. ...... 235/462.46 |
| 5,319,184 A | * | 6/1994 | Gilpin et al. ........... 235/462.43 |
| 5,369,262 A | * | 11/1994 | Dvorkis et al. ............. 345/179 |
| 5,448,050 A | * | 9/1995 | Kostizak ................. 235/462.43 |
| 5,633,489 A | | 5/1997 | Dvorkis et al. .............. 235/472 |
| 5,744,788 A | * | 4/1998 | Metlitsky et al. ........... 235/454 |
| 5,814,804 A | * | 9/1998 | Kostizak ................. 235/472.01 |
| 5,949,068 A | | 9/1999 | Stoner et al. ................ 250/234 |
| 6,000,619 A | * | 12/1999 | Reddersen et al. .... 235/462.43 |
| 6,036,094 A | | 3/2000 | Goldman et al. ........... 235/462 |
| 6,102,293 A | * | 8/2000 | Barkan et al. ............ 235/462.2 |
| 6,186,400 B1 | * | 2/2001 | Dvorkis et al. ......... 235/462.45 |
| 6,315,204 B1 | * | 11/2001 | Knighton et al. ...... 235/462.43 |
| 6,360,949 B1 | * | 3/2002 | Shepard et al. ........ 235/462.37 |

* cited by examiner

Primary Examiner—Michael G. Lee
Assistant Examiner—Steven S. Paik
(74) Attorney, Agent, or Firm—Kirschstein, et al.

(57) ABSTRACT

An optical scanning module and a scanner incorporating the scanning module for reading bar codes and other optical indicia that consists of a printed circuit board, an elongated elliptical aperture in the scanning module that is spaced from the circuit board, a light source mounted on the printed circuit board for projecting at least one beam of light through the aperture and onto a dataform to be read, and a detector mounted on the printed circuit board for sensing light reflected from the dataform and through the aperture. Light baffle is preferably used to isolate light source from the detector in the optical scanning module of the present invention.

14 Claims, 8 Drawing Sheets

LOW COST BAR CODE READER

This patent application claims priority under 35 U.S.C. 119(e) of a provisional application No. 60/144,657 filed on Jul. 16, 1999.

FIELD OF THE INVENTION

This invention relates to the field of optical indicia readers, and more particularly to bar code readers.

BACKGROUND OF THE INVENTION

Electro-optical readers, such as bar code symbol readers, are now quite common. Typically, a bar code symbol comprises one or more rows of light and dark regions, typically in the form of rectangles. The widths of the dark regions, i.e., the bars, and/or the widths of the light regions, i.e., the spaces, between the bars indicate encoded information to be read.

A bar code symbol reader illuminates the symbol and senses light reflected from the coded regions to detect the widths and spacings of the coded regions and derive the encoded information. Bar code reading type data input systems improve the efficiency and accuracy of data input for a wide variety of applications. The ease of data input in such systems facilitates more frequent and detailed data input, for example to provide efficient inventories, tracking of work in progress, etc. To achieve these advantages, however, users or employees must be willing to consistently use the readers. The readers therefore must be easy and convenient to operate.

A variety of bar code readers are known. One type of reader is an optical scanner which scans a beam of light, such as a laser beam, across the symbols. Laser scanner systems and components of the type exemplified by U.S. Pat. Nos. 4,387,297 and 4,760,248—which are owned by the assignee of the instant invention and are incorporated by reference herein—have generally been designed to read indicia having parts of different light reflectivity, i.e., bar code symbols, particularly of the Universal Product Code (UPC) type, at a certain working range or reading distance from a hand-held or stationary scanner. The reader disclosed in the above-listed patents includes a scanning element for moving the laser beam across a bar code symbol. A user aims the reader at a bar code symbol from a position in which the reader is spaced from the symbol, i.e., not touching the symbol or moving across the symbol.

In other scanners where there are no scanning elements, the user must physically move ("swipe") the reader, and the illumination beam, across the bar code. The prior art bar code readers that require physical swiping across bar codes are called "wand" readers. This type of scanning has been done with wand or pen-shaped scanners that are held in the fingers like a writing pen. This type of scanning leads to poor scanning performance because inexperienced users sometimes hold the pen scanner, or a wand, either too perpendicular to the symbol or too tilted, both of which cause reading failures. Wand readers typically use light emitting diodes (LEDs) to illuminate a bar code. To scan the bar code, the user positions the wand reader over the bar code and operates a trigger switch to activate the light source and a signal processing circuitry. Once the light source has been activated, the user swipes the reader over the bar code and the processing circuitry processes the returned signal.

As stated above, these pen-shaped scanners generally use light emitting diodes (LEDs) as a light source and a photodetector (which could be a photo transistor, photodiode or another light detecting component or device) that have their electrical leads soldered to the end of a long narrow circuit board within the pen housing. The bodies of the LED and photodetector are positioned by a support structure in the proper locations as required by the optical system design. Generally, this involves some manual assembly, hand soldering, and in many cases manual alignment. Glue is often used to assure that all components remain in their proper positions throughout the life of the product. These manual operations and adjustments add costs in manufacturing of the pen-shaped scanners and translate into a higher price paid for these bar-code readers by the consumers.

A need for an extremely inexpensive and reliable bar code symbol reader exists for various cost-sensitive scanning applications. These include home shopping by scanning bar codes in printed catalogs, retrieving via the Internet information related to advertised products by scanning bar codes in printed advertisements, programming of electronic games, toys, and appliances, etc.

Generally bar code symbol readers known in the art are too expensive for these applications. Therefore, there is a need for a bar code reader for the use in these applications that does not utilize costly lenses, mirrors, light pipes, optical fibers, optical filters, and other optical components generally found in the bar-code readers currently known in the art.

Another limitation of the bar code symbol readers known in the art, particularly the contact wand bar code scanners, is that they have very limited depth of focus. This is particularly a problem when scanning over a curved surface. The LED illuminates the same part of the symbol that is visible to a photodetector. When the aperture is lifted off the surface, as often happens with curved surfaces, the photodiode can no longer see the area of the symbol that is illuminated, resulting in a scan failure. Therefore, there is a need for a bar code reader with longer depth of field and depth of focus, that is able to scan over the curved surfaces and/or through the thick plastic protective packaging that is used with CDs and other products.

Another shortcoming of the bar code symbol readers known in the art, particularly with contact wand bar code scanners, is that when the stray light (light that is not reflected off a bar code) reaches the photodetector in a reader, it causes a fixed current to be produced by the detector, which adds to the varying current produced by scanning a bar code. This translates to an offset voltage at the output of the current-to-voltage converter. This offset typically varies from unit to unit, and is usually adjusted out or compensated for with a variable resistor that must be adjusted on each individual unit that is built. This manual adjustment process is expensive and undesirable in a low-cost scanner.

SUMMARY OF THE INVENTION

One objective of the present invention is to provide a bar code symbol reader that is inexpensive in production and suitable for home shopping by scanning bar codes in printed catalogs, retrieving via the Internet information related to advertised products by scanning bar codes in printed advertisements, programming of electronic games, toys, and appliances, and other similar applications.

Another objective of the present invention is to provide a low cost bar code symbol reader that eliminates the need for optical components, optical alignment, hand soldering, or gluing of the LED or photodetector.

A further objective of the present invention is to provide a low cost bar code symbol reader that would eliminate read failures due to improper scanner angle with respect to the symbol and improve performance of a scanner when scanning over curved surfaces by extending the depth of focus and depth of field of the scanner with reading aperture that is elongated in a direction perpendicular to the direction the scanner is moved across the symbol.

Another objective of the scanner according to the present invention is to provide a simple design, where the whole tip of the scanner may be replaced, allowing for quick and easy installation and maintenance of the scanner. Additionally, the replaceable tip may come in various sizes and allow the scanner to be adjusted or optimized for scanning of symbols of various different kinds and sizes.

Yet another objective of the present invention is to provide an inexpensive reader (or scanner) that could be incorporated into the same housing as the car alarm control, a remote garage door opener, TV remote controls, portable telephones, personal digital assistants, palm top computers, programmable calculators, pagers, etc.

Another use for the simple reader of the present invention is in improved card readers (commonly called swipe readers), which would allow to read two or more bar codes printed on one card with a single swipe, and to improve the first pass read rate when swiping cards that have damaged symbols.

Another objective is to provide a simple and inexpensive reader that could be used to sense other kinds of markings, such as pencil marks on lottery tickets, school tests, and postal codes.

These and other objectives, characteristic and advantages of the present invention will be disclosed in more detail with reference to the attached drawings.

BRIEF DESCRIPTION OF THE DRAWINGS

FIG. 3 is an exploded cross-sectional view of the scanning module utilized in the embodiment of FIG. 2a;

DETAILED DESCRIPTION OF THE INVENTION

Figure 1A:
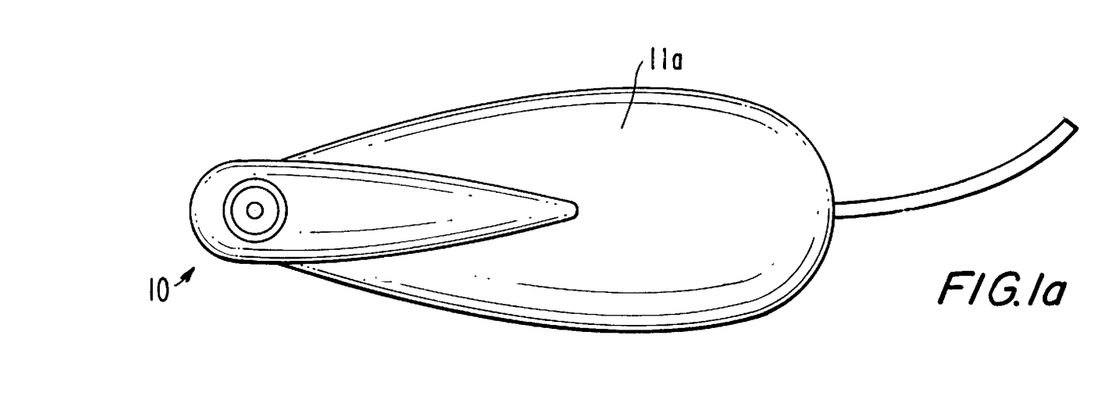
FIGS. 1a and 1b show a top and side views of one embodiment of a bar code reader according to the invention.
Figure 1B:
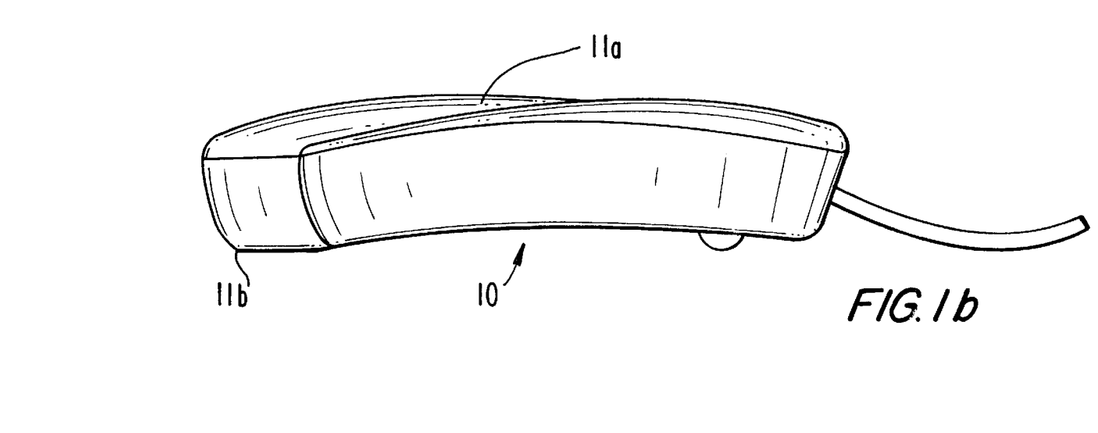

One embodiment of the low-cost bar scanner according to the present invention is illustrated in FIGS. 1a and 1b and comprises a bar scanning device 10 in a shape that is similar to a small mouse pointing device for a personal computer. The scanning device 10 has an outer housing 11 that consists of a lower part 11b and an upper part 11a (a cover). While present invention is not limited to that particular physical shape and other shapes for the low-cost bar scanner according to the present invention are possible, the mouse shape offers several advantages. First, this shape enjoys great recognition and association with high-tech application by the public. Second, the mouse-shaped bar code scanning device of the present invention may also include components of a computer mouse and have an additional use as such. Third, the shape of the housing assures that the scanner is properly oriented with respect to the bar code.

Figure 2A:
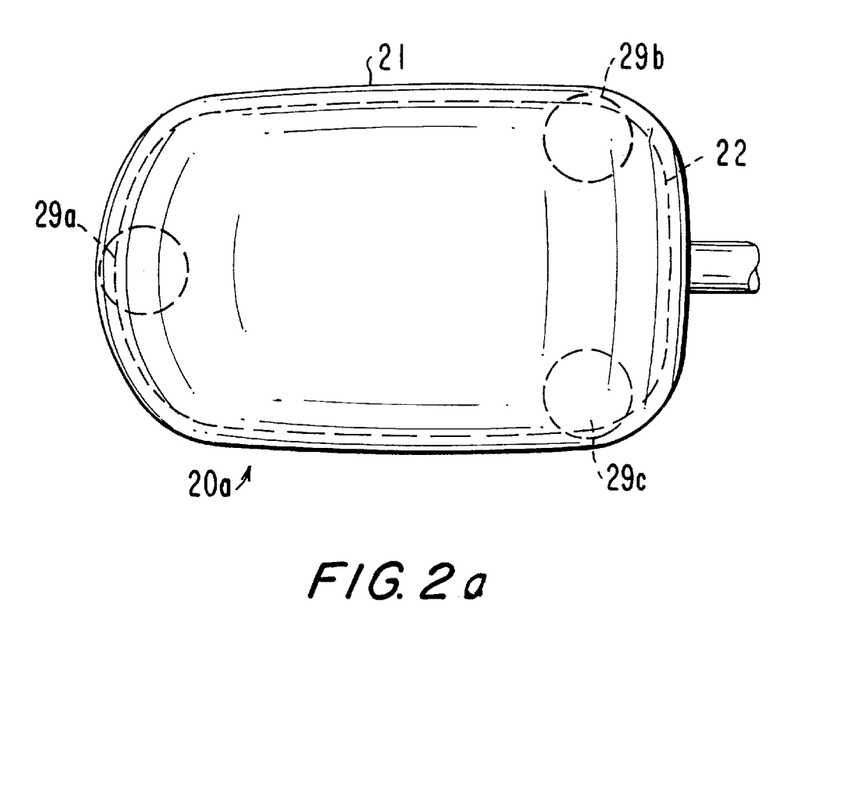
FIG. 2a is a top view of another embodiment of the invention, also showing the outline of the circuit board and the internal components inside the device housing.
Figure 2B:
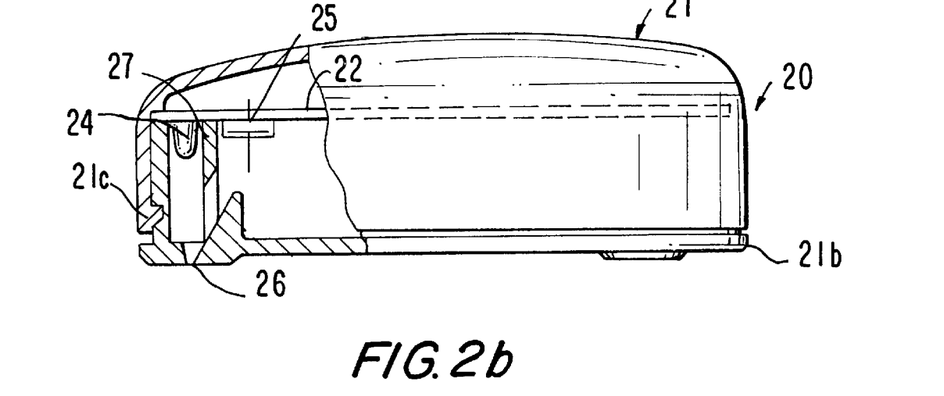
FIG. 2b is a cross sectional view of the device of FIG. 2a, including the internal components inside the device housing.
Figure 2C:
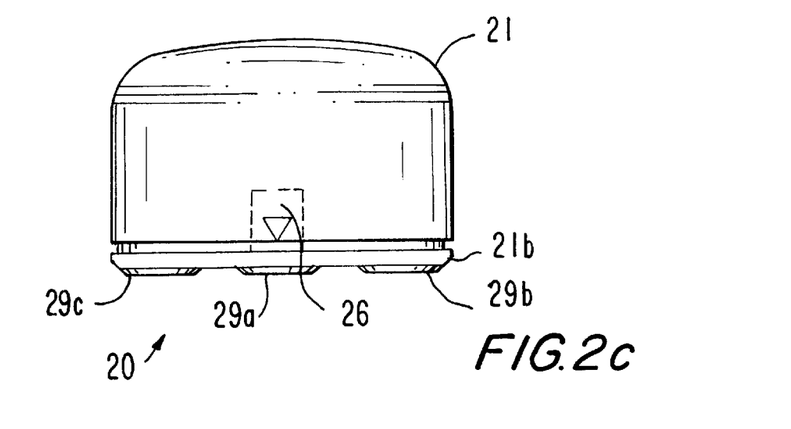
FIG. 2c is a front view of the device of FIG. 2a, including the view of the photodiode window in the interior of the device housing.

FIGS. 2a–2c show an alternative housing design for the bar code scanning device of the present invention. It is understood that the scanner structure inside the housing, shown in FIGS. 2a–2c, can also be used in the embodiment of FIGS. 1a and 1b.

As shown in FIGS. 2a and 2b, the bar scanning device 20 has a housing 21 that holds the circuit board 22 which carries on its underside the surface mounted LED 24 and the photodiode 25, or another type of a photodetector. In an alternative embodiment, the LED (or another light source) and the photodiode may be installed on separate circuit boards that are connected together, or either of them mounted separately on a flex-strip that is soldered to the main board. The surface mounted LED 24 and the photodiode 25 are standard parts that are currently available from several manufacturers. They can be installed on the circuit board with standard pick and place machinery, as are all other electrical components in the scanner. This process is entirely automated and is well known in the electronics industry. No special care is required when placing the photodiode and LED on the board. The position tolerance of standard machinery is adequate.

As further illustrated in FIGS. 2b and 2c, the circuit board 22 of a bar scanning device 20, carrying the photodiode 25, the LED 24, and any other desired circuitry, may be placed into the lower part of the housing 21 with the LED and photodiode on the bottom of the board, aiming downward. Directly below the LED, there is a small aperture 26 in the bottom part 21b of the housing 21. When the LED is illuminated, it projects light towards the bottom of the housing. Some of the light travels through the aperture 26 of the scanning module 200, which is shown in more detail in FIG. 3. The LED 24, which has an integral lens, projects a light beam that diverges at an angle of several degrees. Therefore, even if the LED 24 is tilted slightly when soldered, the aperture will still be illuminated. It is understood that, in accordance with the present invention, the circuit board carrying the photodiode and LED may be placed in the upper part of the housing as well, or any other portion of the housing, so long as it is spaced apart from the aperture.

Figure 3:
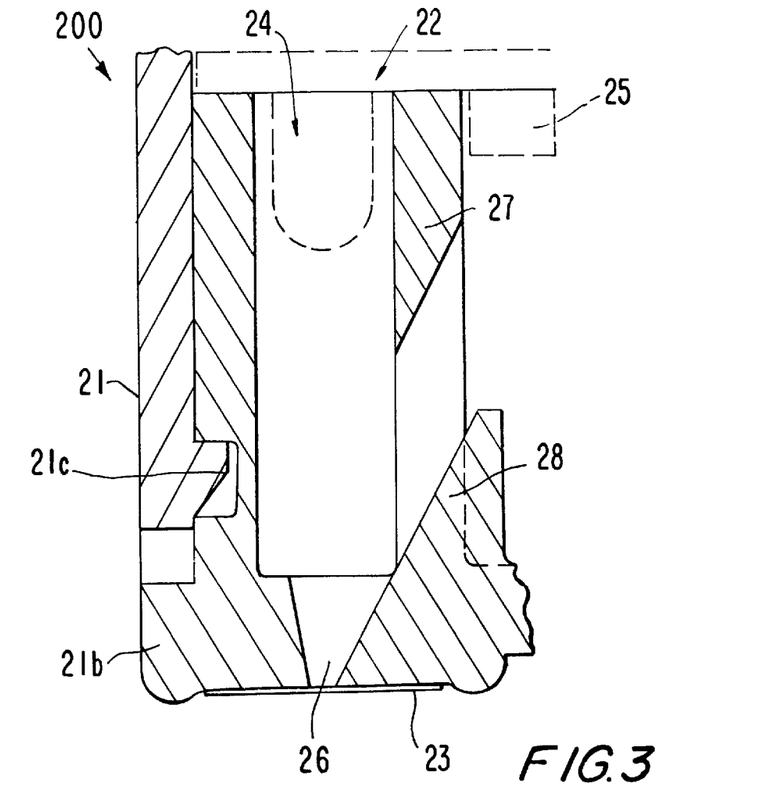

Referring to FIG. 3, the photodiode 25 is positioned on the underside of the circuit board 22 in close proximity to the LED 24. The LED 24 and the photodiode 25, however, are preferably separated by a wall of opaque material, the light baffle 27, which prevents light from passing directly from the LED to the photodiode. This light baffle assures that only light reflected from the bar code (or other type of symbol that is being scanned) can reach the photodiode. The bottom part 21b of the housing 21 should be preferably of a dull black or some other dark color in order to minimize the amount of light reflected back to the detector.

The floor 28 of the bottom part 21b of the scanning module 200 below the detector should be sloped so as to prevent specular reflection of LED light toward the detector. Directly below the LED 24, there is a small aperture 26 in scanning module 200 and the bottom part 21b of the housing 21. In order to avoid being blocked by dirt or debris, the aperture 26 may be covered (for example, on the bottom or outside of the housing) with a thin film of transparent material 23 that acts as an exit window. One of several ways of achieving this is with a transparent self-adhering sticker applied to the bottom of the housing. The sticker could be made with an adhesive free area that is positioned over the aperture.

The optical system of the present invention comprising the LED, photodiode, black-colored bottom part of the housing, light baffle and a small aperture in the bottom part of the housing operates as described below.

Referring to FIGS. 2a, 2b and 2c, the scanner 20 is placed on a symbol to be scanned, with the aperture 26 to one side of the symbol. The user then gently grip the sides of the housing 21 and manually moves it, sliding the aperture 26 entirely across the bar code symbol, so that it crosses every bar and space in the symbol. As the scanner moves, the aperture is sometimes positioned over dark bars in the symbol, and sometimes over light spaces. When positioned over spaces, light from the LED 24 passes through the aperture 26, strikes the space and reflects back through the aperture into the housing. Some of this light strikes the photodiode 25, causing it to produce a current.

In comparison, when the aperture is positioned over a dark bar in the symbol, less light is reflected back into the housing 21 to be received by the photodiode 25, so it produces less current than when the aperture is positioned over a space.

Therefore, the light reflected through the hole will increase and decrease in a pattern determined by the widths of the bars and spaces in the symbol being scanned, as the scanner is moved across the symbol. This varying light causes a corresponding varying current to be produced by the photodiode 25. This current is converted to a varying voltage, amplified and digitized in any of several ways that are commonly used for bar-code scanning. The digitized signal may be sent to a microprocessor (not shown) for decoding.

Alternatively, the amplified varying signal (called the analog signal) can be sent to an analog-to-digital converter or digitizer (not shown). The microprocessor can then process this digital representation of the analog signal to decode the bar code.

The aperture 26 in the bottom part 21b of the housing 21 is preferably around the size of the narrowest bar in any symbol that is to be decoded. It is, however, possible to decode even when the hole is smaller or a little bigger than the bar (or a space between bars).

In another embodiment of the present invention the aperture is elongated in a direction parallel to the bars (i.e. in a direction perpendicular to the direction the scanner is moved across the symbol). This increases signal level, by allowing light to reflect off a larger area of the bar code. By providing an elongated aperture and illuminating a larger area of the bar code, the present invention also enables scanning of a bar code on curved surfaces, where the scanner is slightly lifted off the symbol surface. This improves the field of view of the photodetector and gives the scanner enough depth of focus to scan symbols through the clear plastic cases that are used for example with compact disks. In addition, it reduces scanner's sensitivity to printing defects such as small scratches or dirt on the symbols being scanned.

Figure 5A:
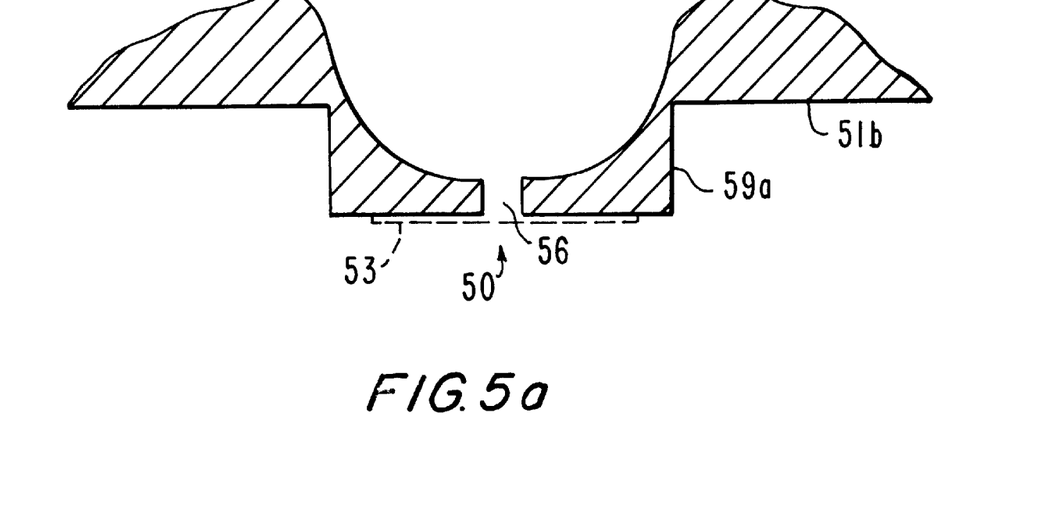
FIGS. 5a and 6a illustrate a scanning operation on curved surfaces with an embodiment of the invention that utilizes flat-bottom feet in the bottom part of the reader housing.
Figure 5B:
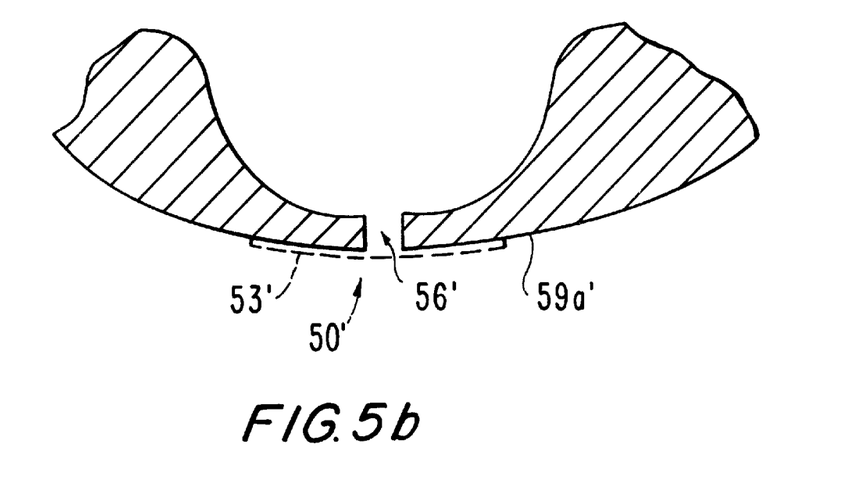
FIGS. 5b and 6b illustrate a scanning operation on curved surfaces with an embodiment of the invention that utilizes sloped bottom-surface feet in the bottom part of the reader housing.
Figure 6A:
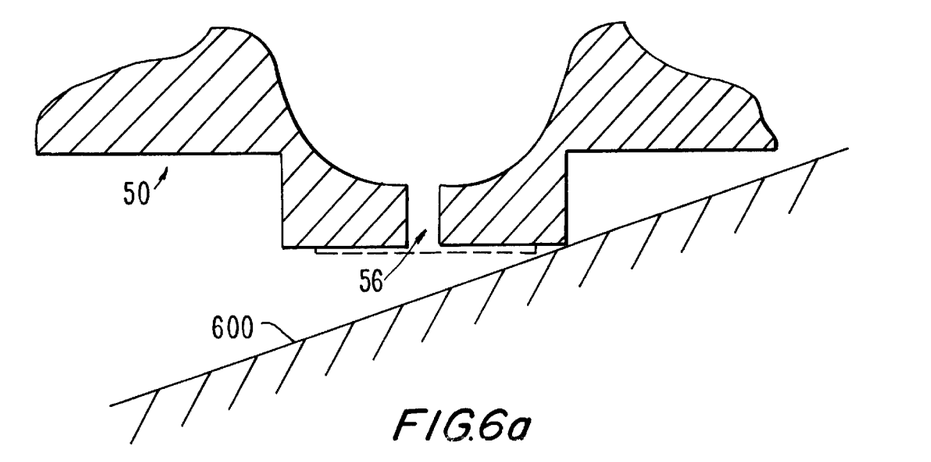
Figure 6B:
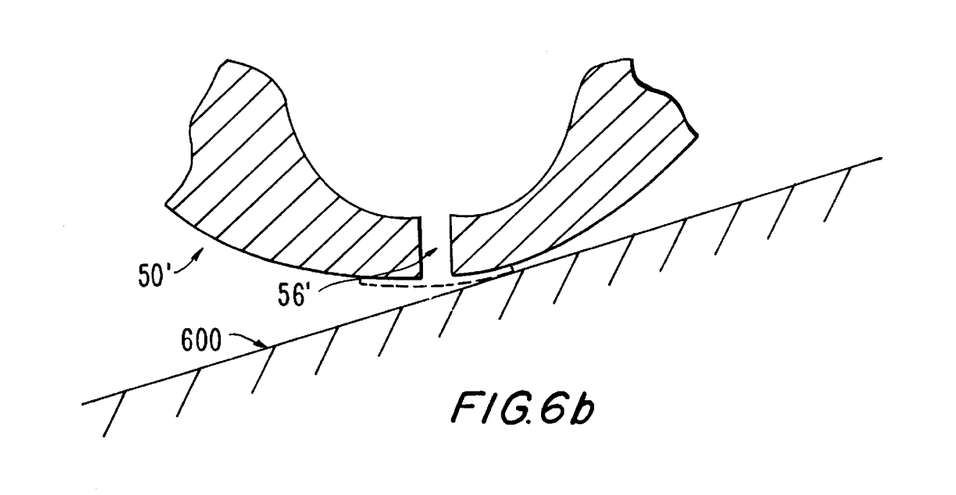

The width of the aperture is preferably around 0.010 to 0.020 inches, and its length is elongated to be around 50% longer than it is wide. In order to avoid being blocked by dirt or debris, the aperture may be covered (for example, on the bottom or outside of the housing) with a thin film of transparent material 23, 53 and 53' that acts as an exit window, as shown in FIGS. 3, 5 and 6, respectively. One of several ways of achieving this is with a transparent self-adhering sticker applied to the bottom of the housing. The sticker could be made with an adhesive free area that is positioned over the aperture.

While many different shapes for the aperture are possible, it is preferable that an elliptical shape is used for the aperture, with the short axis of the ellipse aligned with the direction of travel of the scanner across the bar code. The elliptical shape allows greater angular misalignment, with respect to the direction of travel, than a rectangular aperture would, thereby optimizing the operation of the scanning device.

In the embodiment of the present invention, as illustrated in FIGS. 2a and 2c, the housing 21 has three small protrusions or feet 29a, 29b and 29c on the bottom part 21b of the housing 21. When the scanner is placed on a flat surface, only these three feet touch the surface. Two feet 29b and 29c are preferably located at the end of the housing opposite the scanning aperture, and are spread as far apart as the housing size permits in order to provide stability. The third foot 29a is preferably concentric with the scanning aperture 26. In other words, the scanning aperture 26 projects through the third foot 29a near the center of the foot. When scanning, only these three feet contact the surface of the bar code, or the item carrying the bar code. When scanning a symbol on an uneven (but generally flat) surface, the three feet construction assures that the aperture stays in contact with the symbol and the aperture does not lift away from the surface of the bar code, which would reduce the performance of the scanning device.

Alternatively, the entire bottom part 21b of the scanner housing 21 can be flat, with no protrusions or feet. Since this increases fiction, it is preferably made of a low-friction material.

While other types and color may be used for the housing 21, the bottom part 21b of the housing 21 is preferably injection molded out of black plastic. The lower part of the housing includes the scanning aperture 26, the light baffle 27, and sloping floor area below the photodiode 25. There are also walls, molded as part of the lower housing, that rise up close to or touching the bottom of the circuit board. These walls surround the LED and photodetector excluding ambient light. The walls are preferably made to have a rough texture to minimize internal reflections.

The upper part of the housing 21 may be made of any color that is desired. When the scanner is assembled, the circuit board is placed on locating features integral with the bottom part 21b of the housing 21. Then the upper part (the cover) of the housing is snapped in place. The upper part carries features that hold the circuit board in place. With snaps 21c, shown in FIGS. 2b and 3, that are well known in the art, no screws or glue are necessary to hold the top and bottom of the housing together.

Referring to FIG. 5a, the scanner 50 utilizes flat-surface feet for the scanner, the aperture 56 is in the center of a flat bottom foot 59a extending from the bottom part 51b of the housing. When this embodiment of the invention is used on curved surface, as shown in FIG. 6a, the scanner is tilted with respect to the symbol surface 600, and the reading aperture 56 is lifted off the reading surface, thereby interfering with scanning operation of the device. In another embodiment of the scanner according to present invention, as shown in FIGS. 5b and 6b, the bottom surface of the foot 59a' (and other feet that are not shown) is curved, sloping upward away from the aperture 56'. In this embodiment, the performance of the scanner on curved surfaces is improved, because the reading aperture 56' is not lifted off the symbol surface 600 as much, and remains close to perpendicular relatively to the symbol surface. The sloping surface of the foot 59a' allows scanner to read at tilt angles exceeding 15 degrees.

In an alternative embodiment to that shown in FIGS. 5b and 6b, the entire bottom surface of the scanner housing can be curved, with no protrusions or feet. In order to reduce friction, the bottom surface in such embodiment is preferably made of a low-friction material.

Figure 4A:
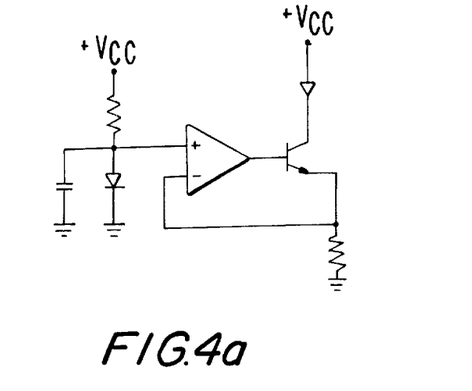
FIG. 4a is an electrical schematic of one embodiment of an LED driving circuit according to the invention.
Figure 4B:
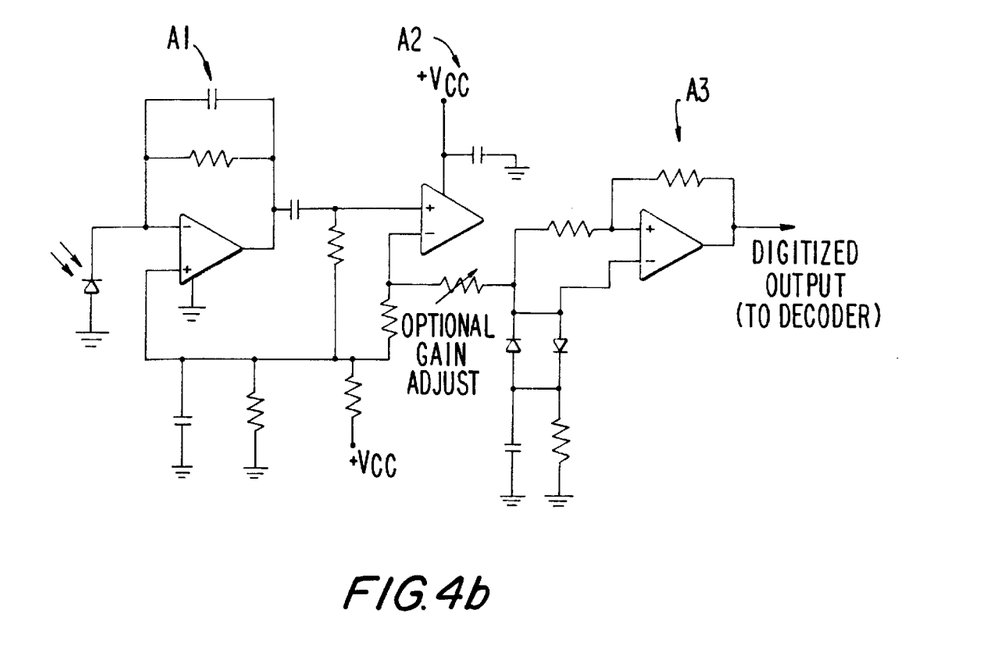
FIG. 4b is an electrical schematic of one embodiment of a signal processing circuit according to the invention.

FIGS. 4a and 4b depict the electrical schematics of a circuit for use with the scanner. FIG. 4a illustrates an LED driving circuit, while FIG. 4b illustrates signal processing circuitry for digitizing the output of the photodiode. The driving circuit of FIG. 4a is generally self-explanatory and easily understood by one skilled in the art. The schematic of FIG. 4b is described below.

The first amplifier stage A1, which is a current-to-voltage converter, is AC coupled into the input of the second stage, which is a voltage amplifier. The AC coupling blocks the DC offset of the first stage, eliminating the need for an offset adjustment. It may still be useful to have a gain adjustment, however, to compensate for variations in signal level due to LED brightness variations. The gain adjustment is done in the second stage A2. The third stage A3 digitizes the signal and outputs it to a decoder. The positive saturation voltage of the third stage op-amp is considered a digital level "1", and the negative saturation voltage of the op-amp is considered a digital level "0". Thus, while the output of the first two stages is analog, the output of the third stage is digital.

The analog circuitry shown can fit entirely on the same side of the circuit board as the LED and the photodiode. This eliminates the expense of placing components on both sides of the board.

The bar code symbol reader (or scanner) of the present invention may be connected by cable to an external decoder and/or power source. Alternatively, a decoder can also be installed on the same board as the analog circuitry. It can have an internal decoder that transmits decoded data to an external host. The reader can be powered by an external power source through the cable, or it can run on internal batteries, that can be either replaceable or rechargeable.

The bar code symbol reader may also be connected to a computer via a serial port. If the serial port is unable to supply power to the scanner, the reader may be powered by batteries held within the housing. The bar code symbol reader of the present invention require very minimal electrical power and can operate for a long period of time powered by small button cells.

Battery-powered embodiments of the bar code symbol reader of the present invention can also be cableless. With these embodiments, the scanned image and/or converted data can be stored in the internal memory residing in the housing of the reader and later downloaded to a host computer. The transmission of the data to the host computer (i.e. downloading) could be accomplished via wireless transmission, such as optical transfer, IR (infra red) transmission, RF (radio frequency) transfer, or with a removable cable plugged into the scanner.

The LED and the photodiode that are used for scanning, may communicate with the scanner (or a bar code symbol reader) in the following manner.

When data stored in the scanner's memory is to be downloaded, the scanner is placed on a special cradle. The cradle positions another LED and a photodiode (or another type of a photodetector) beneath the scanning aperture. The scanner can blink its scan LED to transmit data to the photodiode in the base. The base can blink its LED to transmit data to the photodiode in the scanner.

The scanner can be used in various physical embodiments. When battery powered, it can be in a small housing similar to the small remote car alarm controls people carry on their car keys. It can even be incorporated into the same housing as the car alarm control, or remote garage door opener. The scanner is inexpensive and small enough to be easily incorporated into small appliances such as TV remote controls, portable telephones, personal digital assistants, palm top computers, programmable calculators, pagers, etc.

When used in any battery-powered application, it is necessary to minimize power consumption. In this case, a switch or other form of manual actuator may be provided to turn the scanner on when scanning must occur. When actuated, the analog circuitry, the decoder and the scan LED are activated. The entire system is automatically powered down by the decoder as soon as a decode occurs. If no decode occurs within a predetermined time, power is also shut down. Power can also be immediately shut off, if desired, when the manual actuator is released.

Another use for the scanning system according to present invention is as a card reader (commonly called swipe readers). In this application, a card, such as a credit card, is manually slid through a slot, moving a bar code on the card past the scanning aperture. This scanning system is so inexpensive that two or more of them can be installed in one swipe reader enabling it to read two or more bar codes printed on one card with a single swipe. Alternatively, the two or more scanning apertures can scan different paths across a single bar code with a single swipe. It would only require any one scanning aperture to provide a good scan for decode to be successful. This greatly increases first pass read rate when swiping cards that have damaged symbols.

Multiple rows of scanning apertures (each provided with its own LED and photodetector) can also be used to read two dimensional bar codes such as PDF 417 bar codes printed on cards.

Reading of damaged symbols can be further improved by stitching together data from two or more apertures. One aperture may scan across a defect in one part of a symbol while another aperture scans another defect in another part of the symbol. Neither aperture scans the entire symbol, but the entire symbol can be reconstructed by using data from both apertures.

The simple system described above can also be used to sense other kinds of markings. Pencil marks on lottery tickets or school tests can be sensed. Readers for the postal code used by the U.S. (and other countries) can also be inexpensively read using readers with two or more apertures.

The embodiment of the bar code symbol reader that is shaped like a small computer mouse, is but one possible configuration for a small, inexpensive bar code reader of the present invention. Other configurations are possible. For example, the bar code reader of the present invention may be used in surface-mount packages that aim LED and photodiodes parallel to the plane of the circuit board, as opposed to perpendicular to the plane of the circuit board, as previously described. These side-looking components allow the scanning aperture to be located along the edge of a thin housing, or at the tip of a narrow pen-like housing.

Figure 7:
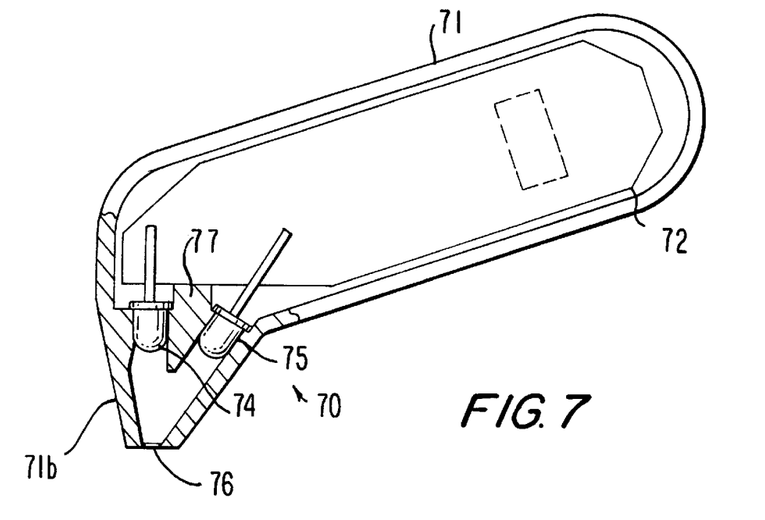
FIG. 7 is a side view of another embodiment of the invention, also showing the outline of the circuit board and the internal components inside the device housing.
Figure 8:
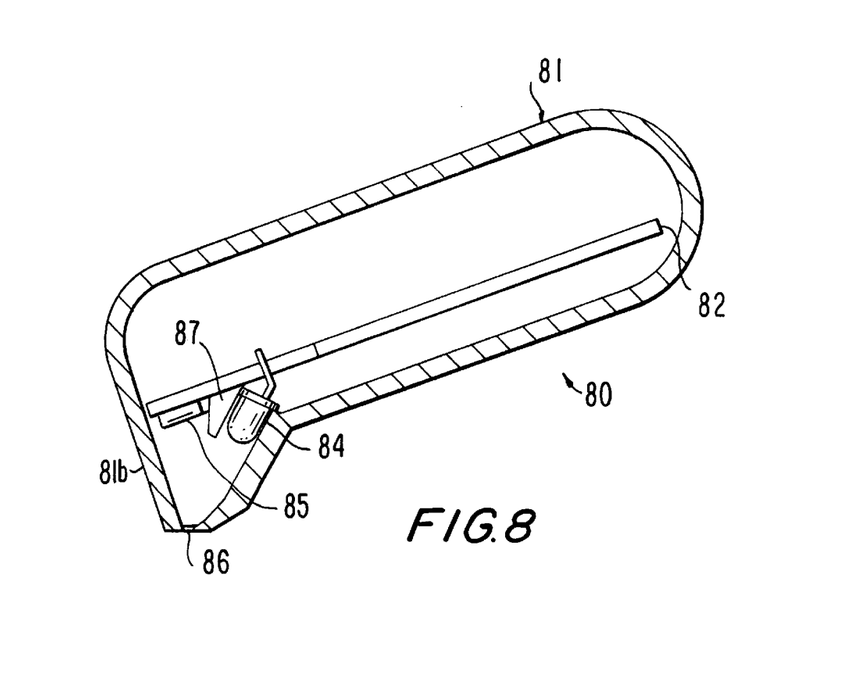
FIG. 8 is a cross sectional view of an alternative embodiment in accordance with present invention, also showing the outline of the circuit board and the internal components inside the device housing.

A cross sectional view of a pistol-shaped wand scanner according to the present invention is illustrated in FIG. 7. The wand scanner 70 comprises a housing 71, that holds the circuit board 72 (PCB board), with LED 74 and photodiode 75 mounted on the circuit board. Directly below the LED 74, there is a small aperture 76 in the neck portion 71b of the wand scanner 70. When the LED is illuminated, it projects light towards the bottom surface of the neck portion 71b. Another embodiment of a pistol-shaped wand scanner according to the present invention is illustrated in FIG. 8, as having the LED 84 and the photodiode 85 mounted on the circuit board 82, over the small aperture 86 in the neck portion 81b of the wand scanner 80. The elongated reading aperture 76 or 86 of the embodiments shown in FIGS. 7 and 8, respectively, allows to maintain proper orientation during the scan, and provides for improved tilt tolerance and depth of focus when reading both flat and curved surfaces. Baffles 77 and 87 in FIGS. 7 and 8 isolate the LEDs from the photodiode as in the previous embodiments.

According to the present invention, the bottom surface of the neck portion may be curved, sloping upward away from the aperture, as described in more detail above, with reference to embodiments shown in FIGS. 5 and 6. Similarly, the performance of the wand scanners in FIGS. 7 and 8 on curved surfaces is improved, because the reading aperture is not lifted off the symbol surface as much during the scan.

Figure 9A:
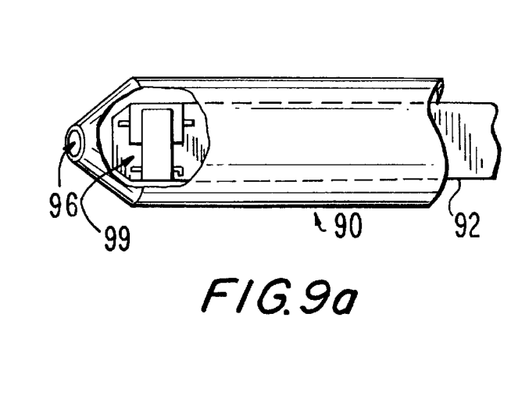
FIGS. 9a, 9b, 9c and 9d show bottom, side and top views of yet another embodiment of the invention, also showing the outline of the circuit board and the internal components inside the device housing.
Figure 9B:
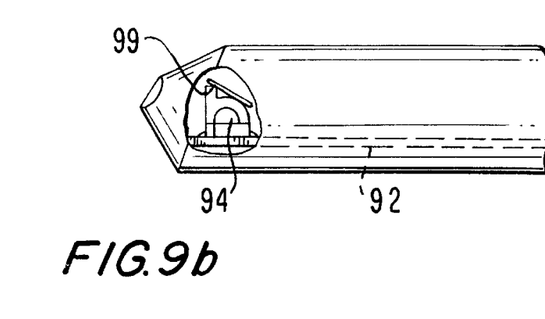
Figure 9C:
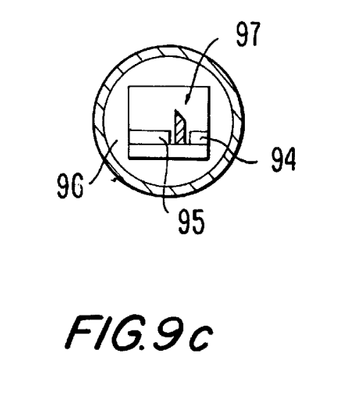
Figure 9D:
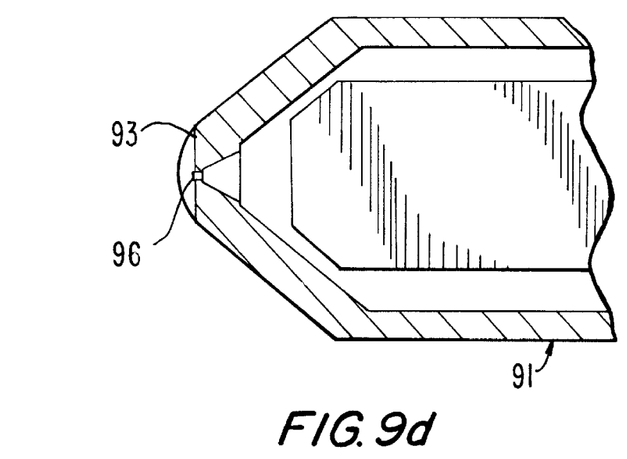

Another type of scanner 90 in accordance with the present invention is illustrated in FIGS. 9a, 9b, 9c and 9d, showing bottom, side, top and detail views, respectively, of a pen-type scanner. The LED 94 and the photodiode 95, separated by the baffle 97 are mounted on the circuit board 92. This embodiment also comprises a fold mirror 99 that directs light through the aperture 96. Light from the LED 94 is reflected by the fold mirror 99 through the aperture 96, and reflected light is directed by the mirror 99 to the photodiode 95. The aperture 96 may be protected by a transparent tape 93 that is inserted into the tip of the scanner over the aperture 96 as shown in FIG. 9d.

The scanners according to the present invention may utilize a thin film of transparent material, such as for example a transparent self-adhering sticker applied to the bottom of the housing, or inserted into the scanner tip over the aperture, for the purpose of preventing blockage of the aperture by dirt or debris. When the protective tape wears out or becomes damaged, the tape may be replaced either by the user himself or at a service depot.

Alternatively, the whole tip of the scanner may be replaced, allowing for quick and easy installation and maintenance of the scanner. Additionally, the replaceable tip may come in various sizes and allow the scanner to be adjusted or optimized for scanning of symbols of various different kinds and sizes.

As another alternative, a small piece of a transparent substance, such as for instance plastic or glass, may be installed over or in the aperture instead of the tape.

Although the invention has been described with reference to the specific embodiments, it will be apparent to one skilled in the art that variations and modifications are contemplated within the spirit and scope of the invention. The drawings and description of the specific embodiments are made by way of example rather than to limit the scope of the invention, and it is intended to cover within the spirit and scope of the invention all such changes and modifications.

What is claimed is:

1. A bar code reader for electro-optically reading a bar code symbol on a target, comprising:

a) a housing having a bottom wall facing the target, and configured to be held and slidably moved by a user across the target, during reading;

b) a plurality of feet on, and extending from, the bottom wall for slidably engaging the target during the sliding movement of the housing;

c) a printed circuit board within the housing above the bottom wall;

d) an aperture extending through the bottom wall;

e) a light source on the board for emitting light toward the bottom wall and through the aperture for reflection from the symbol on the target;

f) a detector on the board for detecting light reflected from the symbol, and for generating an electrical signal corresponding to the symbol; and g) said aperture extending through one of the feet for positioning the aperture over the symbol during the sliding movement of the housing.

2. The reader of claim 1, wherein the light source is a light emitting diode.

3. The reader of claim 1, wherein the light source is a laser diode.

4. The reader of claim 1, wherein the detector is a photodiode.

5. The reader of claim 1, wherein the housing has a bottom part connected to a cover part, and wherein the parts are configured to be received within a palm of a hand of the user.

6. The reader of claim 1, wherein the light source and the detector are mounted in a side-by-side relationship on a lower surface of the board.

7. The reader of claim 6, and comprising a light baffle between the light source and the detector.

8. The reader of claim 1, wherein said one of the feet has a circular configuration, and wherein the aperture is a circular opening concentric with said one of the feet.

9. The reader of claim 1, wherein there are three feet in number, and wherein two of the feet are located at one end region of the housing, and wherein said one of the feet is located at an opposite end region of the housing.

10. The reader of claim 1, wherein each of the feet has a substantially planar slide surface.

11. The reader of claim 1, wherein each of the feet has a curved slide surface.

12. The reader of claim 1, wherein the aperture is bounded by inclined boundary walls that converge toward each other in a direction away from the light source.

13. The reader of claim 1, wherein the aperture has an elongated cross-section.

14. The reader of claim 1, and comprising a light-transmissive window that covers the aperture.

* * * * *